United States Patent [19]

Chronister

[11] Patent Number: 5,474,450
[45] Date of Patent: Dec. 12, 1995

[54] DENTAL INSTRUMENT

[76] Inventor: Stephen H. Chronister, 627 SW. Topeka Blvd., Topeka, Kans. 66603

[21] Appl. No.: 193,545

[22] Filed: Feb. 8, 1994

[51] Int. Cl.[6] ................................................. A61G 17/02
[52] U.S. Cl. ................................. 433/80; 433/85; 604/30
[58] Field of Search .................................. 433/80, 82, 85, 433/87, 91, 93, 94, 95, 96; 604/30, 35, 33, 34, 902

[56] References Cited

U.S. PATENT DOCUMENTS

| | | | |
|---|---|---|---|
| 1,114,268 | 10/1914 | Kells | 604/902 X |
| 2,804,075 | 8/1957 | Borden | 604/902 X |
| 2,812,765 | 11/1957 | Tofflemire | 604/902 X |
| 3,109,426 | 11/1963 | Noonan et al. | 604/33 |
| 3,208,145 | 9/1965 | Turner | 604/902 X |
| 3,727,310 | 4/1973 | Baker . | |
| 3,949,748 | 4/1976 | Malmin | 433/91 X |
| 4,215,476 | 8/1980 | Armstrong | 433/80 |
| 4,291,691 | 9/1981 | Cabal et al. | 604/902 X |
| 4,340,365 | 7/1982 | Pisanu | 433/80 |
| 4,397,640 | 8/1983 | Haug et al. | 604/35 X |
| 4,560,373 | 12/1985 | Sugino et al. | 604/30 |
| 4,680,026 | 7/1987 | Weightman et al. . | |
| 4,708,717 | 11/1987 | Deane et al. | 604/35 |
| 4,872,837 | 10/1989 | Issalene et al. | 433/29 |
| 4,874,364 | 10/1989 | Morris et al. | 604/35 |
| 5,061,180 | 10/1991 | Wiele | 433/91 |
| 5,306,237 | 4/1994 | Clement et al. | 604/30 |

Primary Examiner—Nicholas D. Lucchesi
Attorney, Agent, or Firm—Litman, McMahon and Brown

[57] ABSTRACT

A dental instrument including separable spray and suction mechanisms. The spray mechanism is preferably an air and water syringe of the type conventionally found in a dentist office. The spray mechanism has an elongate nozzle. The suction mechanism includes a tubular structure joined to a valve which is in turn joined to a suction or vacuum source. The tube includes an interior passageway and a forward suction opening into the passageway. The tube also includes a bend and has an aperture at the bend for removeably receiving the spray nozzle. In this manner the spray nozzle can be selectively inserted within the passageway of the suction mechanism. A user is then able to actuate either the spray mechanism and/or the suction mechanism utilizing a single hand that is holding the instrument 1. Alternatively, the mechanism may be removed from the suction mechanism and be utilized as an independent tool.

3 Claims, 2 Drawing Sheets

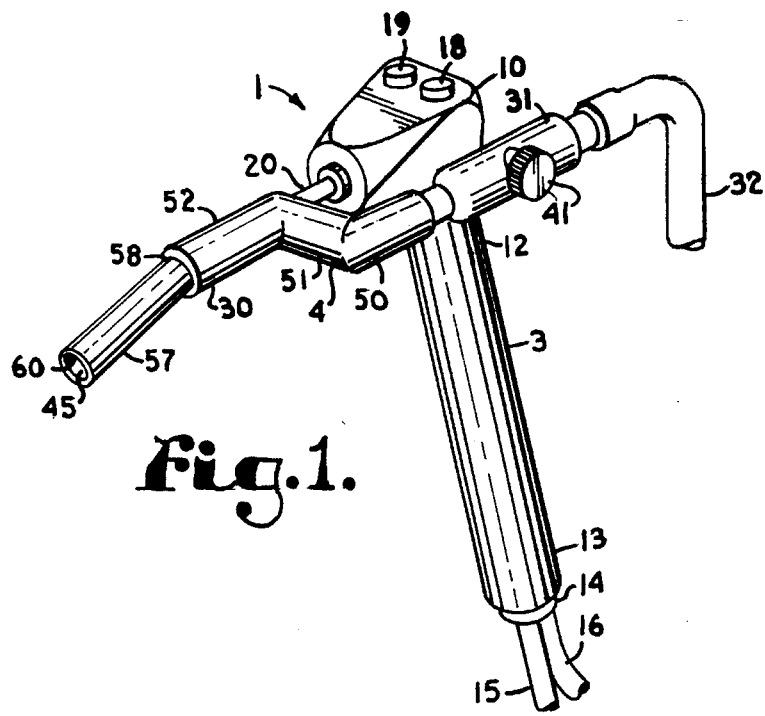
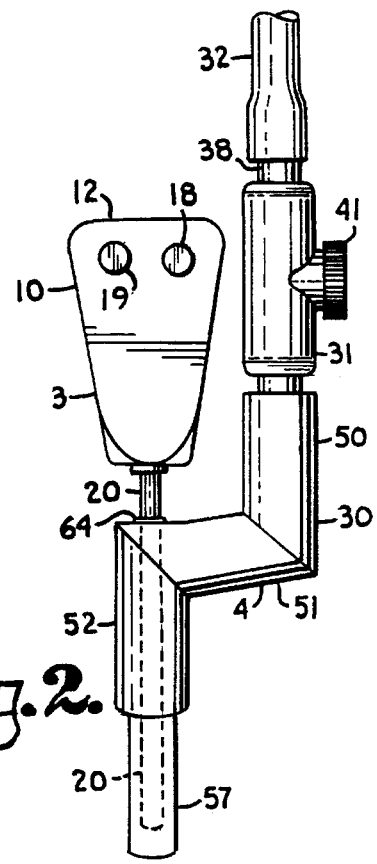
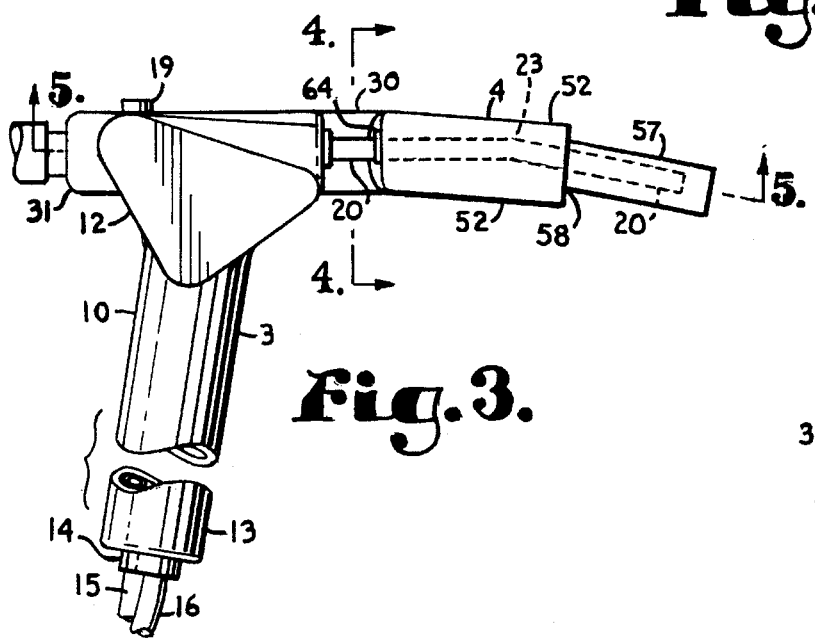
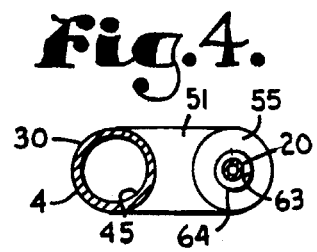
Fig. 1.
Fig. 2.
Fig. 3.
Fig. 4.

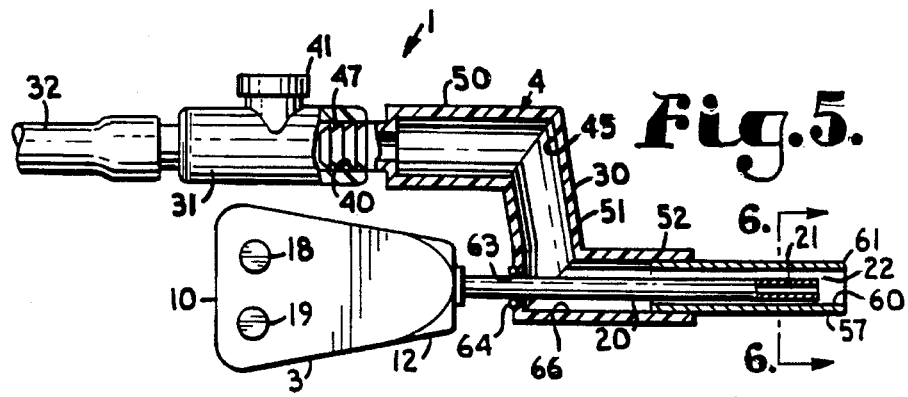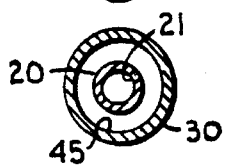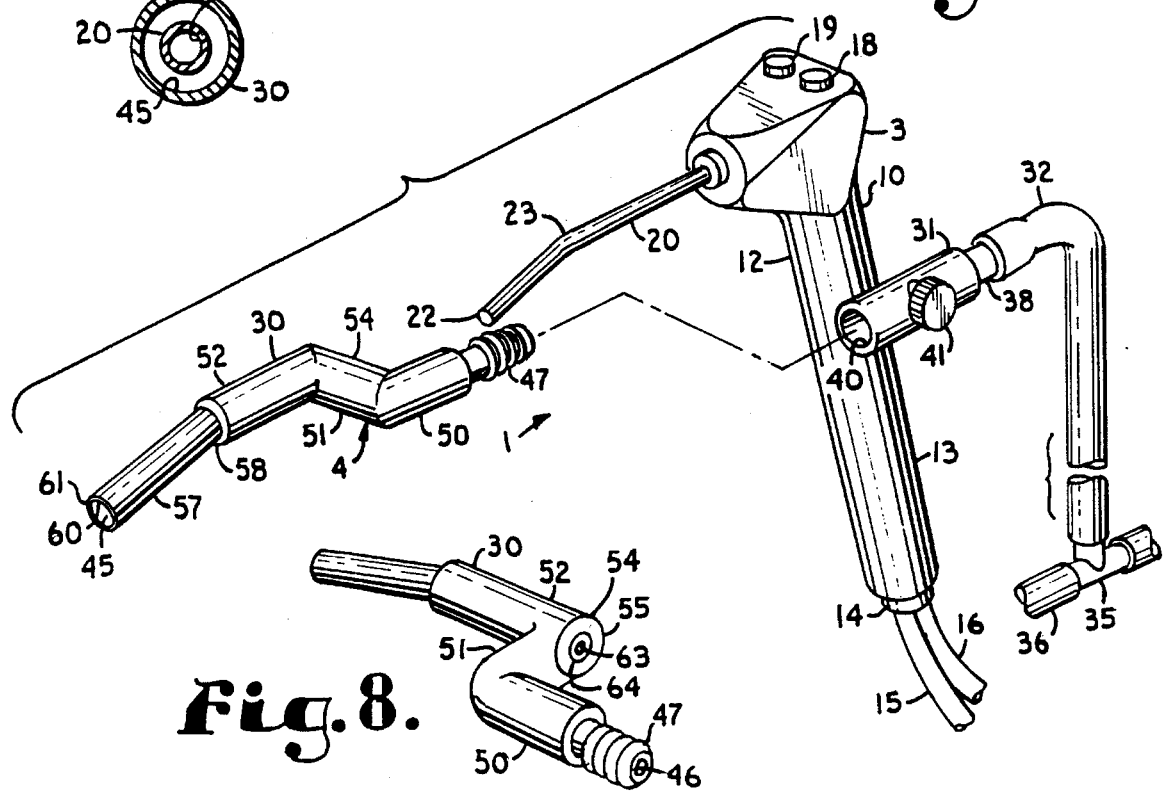

DENTAL INSTRUMENT

BACKGROUND OF THE INVENTION

The present invention is directed to an instrument for use by dentists or the like which allows the removable combination of an air and water syringe with a suction mechanism so that both can be used in combination and with a single hand or separated for individual use.

Two essential tools which are found in virtually every dentist office are an air and water syringe which allows the selective spray of air and/or water in the mouth of the patient and a suction apparatus which withdraws liquid from the patient's mouth. These two devices are normally independent of one another which produces a number of problems during usage. In particular, although it is sometimes preferable to have each of the devices in a separate hand for usage, it is common for a dentist to need both devices at the same time as one of the dentist's hands is required for conducting some procedure or working with some other tool. This presents a problem, since conventional instruments of this type are not designed to be held and operated in combination in a single hand.

Prior art devices have been developed to overcome this problem. However, the prior art devices essentially place the air and water spray mechanism and suction mechanism together in a single tool which is inseparable into component parts. Furthermore, these combination tools tend to be rather complicated and expensive as compared to conventional devices of this type. Yet further, the prior art devices require the complete replacement of conventional dentist devices of this type with the new combined tool.

Consequently, it is desirable to be able to provide an instrument that includes a suction device with an air and water spray mechanism in such a manner that they can be easily joined together or used separately. Still further it is desirable that the apparatus be controllable by a single hand leaving the opposite hand of the dentist free for other purposes. In addition it is desirable for the instrument to meet conventional sterile requirements which means each piece that engages the patient should be able to be easily sterilized. Finally, it is desirable that the instrument take advantage of as much existing standard equipment as possible and, in particular, that it utilize a conventional air and water spray syringe of the type found on the dental unit in virtually every dentist's office.

SUMMARY OF THE INVENTION

The present invention is directed to an easily disassembled combination of a dental water dispensing mechanism, especially an air and water dispensing syringe, and a suction mechanism. When combined and joined in a piggy back fashion, the overall instrument is holdable, as a single unit, in a single hand and fully controllable with the hand which holds it.

Preferably, the water mechanism is a standard air and water dispensing syringe which is found in most dental offices as a part of a conventional dental unit (that is, the equipment purchased for most dental examination rooms and sold as an overall unit by several suppliers). The water dispensing mechanism includes a water dispensing nozzle, a handle and a pair of finger actuated valves for dispensing water and/or air through the nozzle.

The suction mechanism includes a suction valve attached to a suction generating conduit and having an elongate tube attached thereto. The tube includes an interior passageway and at least one intermediate bend. The tube also has a pliable suction tip mounted on the front end thereof with a opening leading to an internal suction passageway that is controlled by the suction valve. Located at the bend in the tube is an aperture with sealing apparatus which allows the aperture to removeably receive and seal about the water dispersing mechanisms nozzle. In this manner the water dispersing mechanisms nozzle may be selectively mounted within the suction passageway and extends to near the opening of the suction passageway such that a user thereof may alternatively operate the various valves of the device to provide any combination of suction, water and air at the opening of the suction passageway.

The tube is preferably constructed of a disposable material and removable from the valve so that a new tube can be used for each patient. The water dispensing mechanism is selectively either mounted piggy back style upon the suction mechanism as described above so that the two can be utilized in combination or alternatively can be easily removed so that each may be used independent of one another and operated by separate hands, if so desired.

OBJECTS AND ADVANTAGES OF THE INVENTION

Therefore, the objects of the present invention are: to provide a dental instrument which combines a water dispensing mechanism with a suction mechanism into a single and easily disassembled unit that can be operated by a single hand of a user; to provide such an instrument which utilizes a conventional dental air and water syringe as the water dispensing mechanism; to provide such a instrument wherein the water dispensing mechanism is piggy backed on the suction mechanism and wherein a nozzle of the water dispensing mechanism penetrates into an interior suction passageway of the suction mechanism, so that an opening of the water dispensing mechanism is positioned in close proximity to a suction opening of the suction mechanism; to provide such an instrument wherein a portion of the suction mechanism is disposable and can be easily removed and replaced by a new unit for each patient; to provide such an instrument wherein the water dispensing mechanism can be very simply and conveniently separated from the suction mechanism during various procedures so that the two component parts can be alternatively used together or in separate hands as needed during various procedures; to provide such an instrument which is relatively inexpensive to produce and makes utilization of a conventional and preferably previously existing air and water dental syringe in the construction thereof which does not require repurchase; to provide such an instrument which is relatively easy to use, simple to construct and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a dental instrument in accordance with the present invention illustrating a combined air and water syringe and vacuum suction mechanism.

FIG. 2 is a top plan view of the instrument with interior portions thereof illustrated by phantom lines.

FIG. 3 is a side elevational view of the instrument with certain interior detail shown in phantom lines.

FIG. 4 is a cross sectional view of the instrument, taken along line 4—4 of FIG. 3.

FIG. 5 is a cross sectional view of the instrument, taken along line 5—5 of FIG. 3.

FIG. 6 is a cross sectional view of the instrument, taken along line 6—6 of FIG. 5.

FIG. 7 is a perspective and exploded view of the instrument illustrating the water dispensing mechanism removed from the suction mechanism and further illustrating the removal of the forward disposable suction tube from a remainder of the suction mechanism.

FIG. 8 is a perspective view of the disposable tube of the suction mechanism.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 designates a dental instrument including a spray mechanism 3 and a suction mechanism 4.

The spray mechanism 3 preferably includes a conventional air and water syringe 10 of the type that is typically found associated with dental units found in most dental offices and is readily available from most dental equipment supply business. The syringe 10 includes a body 12 having a depending handle 13. Connected to a lower end 14 of the handle and extending therethrough is a air hose 15 and a water hose 16. The hoses 15 and 16 are connected to sources of compressed air and water (not shown).

Located near the upper end of the syringe 10 is an air actuator 18 and a water actuator 19. The actuators 18 and 19 have associated therewith respective valves which are flow connected to respective hoses 15 and 16. A spray dispersion nozzle 20 is secured to the front end of the body 12 near the upper end thereof and includes an internal passageway 21 ending in a distal spray opening 22. The nozzle 20 is relatively elongate and is somewhat bent at a bend 23 therealong. The passageway 21 is flow connected to the valves of the actuators 18 and 19 so as to receive air and/or water into the passageway 21 when one or both of the actuators 18 and 19 are actuated.

The suction mechanism 4 includes a tube 30, a valve 31 and conduit means such as hose 32. The hose 32 is joined to a juncture tee 35 which in turn connects a vacuum hose 36. The vacuum hose 36 is preferably a conventional hose used in the practice of dentistry into which the tee 35 and subsequent elements of the section mechanism 4 have been added by cutting and insertion. The hose 32 is joined to the valve 31 at a nipple 38 so as to effectively flow connect suction or vacuum within the vacuum hose 36 to the one side of the valve 31. In this manner the hose 32 and hose 36 function to operable join the valve 31 to vacuum generating means, such as a vacuum compressor or blower (not shown).

Passing through the valve 31 is a passageway 40 through which flow is controlled by control knob 41.

The tube 30 contains an internal suction passageway 45 having a first opening 46. Surrounding and in close proximity to the opening 46 is a serrated nipple which is sized and shaped to be snugly received within the valve passageway 40 so as to effectively seal therewith. The nipple 47 and valve 31 are constructed such that the nipple 47 along with its attached tube 30 are relatively easily removed from and inserted into the passageway 40.

The tube 30 has a substantially Z-shaped configuration having a first portion 50 attached to the nipple 47, a second portion 51 aligned at slightly less than a 90° angle relative to the first portion 50 and a third portion 52 which is again aligned at slightly less than a 90° angle with respect to the second portion 51 and parallel to the first portion 50. In this manner a bend 54 is constructed between the second portion 51 and the third portion 52 and forms a seat 55 thereat. The third portion 52 further includes a forwardly extending suction tip 57 which is typically constructed of pliable plastic or rubber so that it will bend relatively easy should it engage a patient. The suction tip 57 is angled slightly with respect to the third portion 52 so as to have a bend 58. The angle at the bend 58 is relatively comparable to the angle of the bend 23 of the water spray nozzle 20.

The passageway 45 extends entirely through the tube first portion 50, second portion 51 and third portion 52, including the suction tip 57 and opens to the exterior at a suction opening 60 at the front end 61 of the suction tip 57.

Positioned in the seat 55 is an aperture 63 having sealing means thereabout, such as an illustrated o-ring 64 positioned. The aperture 63 is sized and shaped so as to receive the nozzle 20 and the o-ring 64 is also sized and shaped to receive the nozzle 20 and seal thereabout.

The spray mechanism 3 has a mounted position or configuration relative to the suction mechanism 4 which is shown in FIGS. 1 through 6 wherein the spray mechanism 3 is piggybacked on the suction mechanism 4 and the nozzle 20 is sheathed or received within the passageway 45. In particular, the spray nozzle 20 of the spray mechanism 3 is inserted through the aperture 63 and extends through the passageway 45 to near the forward or distal end thereof. In this manner the spray opening 22 of the spray mechanism 3 is located in close proximity to the suction opening 60 of the suction mechanism 4. This is seen in FIGS. 2, 3 and 5. The suction passageway 45 in the region of the tube third portion 52 and suction tip 57 is substantially larger than the diameter of the nozzle 20 so as to define and provide an annular suction passage 66 around the nozzle 20.

The spray mechanism 3 also has a non-mounted or separated configuration with respect to the suction mechanism 4 which is illustrated in FIG. 7 with the further separation of the tube 30 from the valve 31. In the non-mounted configuration the spray mechanism 3 is separated from the suction mechanism 4 and both mechanisms 3 and 4 can be used separately. The instrument 1 can thus be easily and rapidly switched from between the mounted configuration and the non-mounted configuration to allow a user to take full advantage of the apparatus.

When the apparatus is in the mounted configuration, such as is seen in FIGS. 1 through 6, the valve control knob 1 for suction and the actuators 18 and 19 for air and water respectively are located so that a user holding the instrument 1 by the handle 13 can easily operate each utilizing the same hand as is being used to hold the instrument 1.

The tube 30 is preferably constructed of a plastic material or the like and is disposable. This eliminates the need to sterilize the tube 30 after each usage. For replacement of the tube 30, the spray mechanism 3 is withdrawn from the suction mechanism 4, such as is shown in FIG. 7. The tube 30 is then separated from the valve 31 by withdrawing the nipple 47 from the passageway 45 and replacing the removed tube 30 with a new tube of identical or similar construction.

Although the instrument 1 is described as a dental instrument, it is foreseen that it could be utilized for certain other purposes, including but not limited to, medical practices requiring both water spray and vacuum or suction.

In use a dentist may use the spray mechanism 3 and suction mechanism 4 separately and in separate hands by actuation of the control knob 41 on the suction mechanism 4 or actuators 18 and 19 on the spray mechanism 3. If the user so desires, the spray mechanism 3 may be used in conjunction with a conventional vacuum hose (not shown) for such two handed procedures. If the user needs one of their hands to either conduct some procedure or utilize some other tool, the separable parts of the instrument 1 may be joined together by inserting the nozzle 20 of the spray mechanism 3 into and through the aperture 63 of the suction mechanism 4 until the spray opening 22 is in close proximity to the suction opening 60, as is seen in FIGS. 2, 3 and 5. The user then may selectively use any or all of the air actuator 18, water actuator 19 and suction control knob 41 to provide a desired combination of air spray, water spray and vacuum or suction of liquid.

It is to be understood that while certain forms of the present invention have been illustrated and described herein, it is not to be limited to the specific forms or arrangement of parts described and shown.

What is claimed and desired to be secured by Letters Patent is as follows:

1. A dental instrument comprising:
   a) a water spray mechanism flow connectable to a water supply and having a user operable water valve for controlling flow of water therethrough;
   b) a water distribution nozzle on said spray mechanism having an internal fluid passageway flow connected to said water valve;
   c) a suction mechanism; said suction mechanism including a suction passageway flow connected to a suction control valve that in turn is flow connectable to a suction generating source; said suction mechanism including a mounting aperture to allow said water distribution nozzle to be selectively and removeably inserted through said aperture, said water spray mechanism having a mounted position, such that when in the mounted position, said water nozzle is at least partially located within said vacuum passageway; said water spray mechanism having a non-mounted position wherein said water spray mechanism and said suction mechanism are unjoined and separably usable;
   d) said water spray mechanism includes a handle and said water distribution nozzle is flow connected to an air source;
   e) said spray mechanism further includes a valve for the control of air into said water distribution nozzle fluid passageway; and including
   f) water source means connected to said water valve and suction generating means connected to said suction control valve.

2. A dental instrument comprising:
   a) an air and water spray syringe having a handle, an elongate spray nozzle with a distal spray opening, a handle for holding, an air valve and a water valve flow connected to said spray opening and piping means operably connecting said air and water valve to sources of air and water respectively;
   b) a suction apparatus having a valve flow connectable to a suction generator and a suction tube joined to the suction valve; said suction tube having a distal end with a suction opening therein flow connected to a suction passageway that is in turn flow connected to said suction valve; said tube having a bend therein; said tube having an aperture at said bend that opens into said passageway and is sized to receive said spray nozzle; said aperture including sealing means for pliably sealing about said spray nozzle; said tube being disposable and including connecting means for removeably connecting said tube to said suction valve; and
   c) said syringe having a mounted position wherein said syringe is removeably mounted with said spray nozzle positioned in said passageway with said passageway having a larger interior diameter than said nozzle to allow flow thereby and a non-mounted configuration wherein said syringe is separated from and independently usable relative to said suction apparatus.

3. The instrument according to claim 2 wherein:
   a) said tube includes a pliable suction tip; and
   b) said spray opening and said suction opening are located in close proximity when in the mounted configuration.

\* \* \* \* \*